(12) United States Patent
Screen et al.

(10) Patent No.: US 8,563,753 B2
(45) Date of Patent: Oct. 22, 2013

(54) MICROENCAPSULATED CATALYST

(76) Inventors: Thomas Eric Oliver Screen, Blackley (GB); Mohammed Nisar, Blackley (GB)

( * ) Notice: Subject to any disclaimer, the term of this patent is extended or adjusted under 35 U.S.C. 154(b) by 0 days.

(21) Appl. No.: 13/147,285

(22) PCT Filed: Feb. 12, 2010

(86) PCT No.: PCT/GB2010/050225
§ 371 (c)(1),
(2), (4) Date: Sep. 29, 2011

(87) PCT Pub. No.: WO2010/094946
PCT Pub. Date: Aug. 26, 2010

(65) Prior Publication Data
US 2012/0016139 A1    Jan. 19, 2012

(30) Foreign Application Priority Data
Feb. 18, 2009   (GB) .................................. 0902634.5

(51) Int. Cl.
*C07D 319/06*   (2006.01)

(52) U.S. Cl.
USPC ........... 549/373; 502/159; 564/417; 564/385; 568/318

(58) Field of Classification Search
None
See application file for complete search history.

(56) References Cited

U.S. PATENT DOCUMENTS 3,954,666 A    5/1976   Marquisee et al.

FOREIGN PATENT DOCUMENTS

WO    WO-03/006151    1/2003

OTHER PUBLICATIONS

International Search Report and Written Opinion mailed Aug. 26, 2010 for International Application No. PCT/GB2010/050225 (12 pages).
International Preliminary Report on Patentability mailed May 20, 2011 for International Application No. PCT/GB2010/050225 (9 pages).
Ramarao et al. "Encapsulation of Palladium in Polyurea Microencapsules," Chem. Commun. pp. 1132-1133 (Apr. 23, 2002).
Yu et al. "Transfer Hydrogenation Using Recyclable Polyurea-Encapsulated Palladium: Efficient and Chemoselective Reduction of Aryl Ketones," Chemical Communications—ChemCom, Royal Society of Chemistry, pp. 678-679 (Jan. 1, 2003).
Ley et al., "Recyclable Plyurea-Microencapsulated Pd(0) Nanoparticles: An Efficient Catalyst for Hydrogenolysis of Epoxides," Organic Letters, American Chemical Society, vol. 5, No. 24, pp. 4665-4668 (Jan. 1, 2003).
Reaxa: "Pd(0) EnCat™ NP30, Hydrogenation & Transfer Hydrogenation User Guide," pp. 1-20, URL: http://www.reaxa.com/documents/reaxa_pd0_encat_30np_user_guide_2006.pdf> (Apr. 2006).
Hagio et al., "Practical Preparation Method of Polymer-Incarcerated (PI) Palladium Catalysts Using Pd(II) Salts," Organic Letters, American Chemical Society, vol. 8, No. 3, pp. 375-378 (Feb. 2, 2006).
Akiyama et al., "The Polymer Incarcerated Method for the Preparation of Highly Active Heterogeneous Palladium Catalysts," J. of Amer. Chem. Soc., vol. 125, pp. 3412-3413 (Jan. 1, 2003).

*Primary Examiner* — Yun Qian
(74) *Attorney, Agent, or Firm* — Bingham McCutchen LLP

(57) ABSTRACT

The present invention relates to a catalyst system. In particular the invention relates to a catalyst in the form of metal or an alloy that is encapsulated within a polymer shell or matrix. More specifically the invention is directed towards reactive catalytic metals that may be pyrophoric or otherwise reactive in air and/or susceptible to oxidation. In particular, the invention is concerned with catalysts based on nickel.

6 Claims, No Drawings

MICROENCAPSULATED CATALYST

This application is the U.S. national stage application of International (PCT) Patent Application Serial No. PCT/GB2010/050225, filed Feb. 12, 2010, which claims the benefit of GB Application No. 0902634.5, filed Feb. 18, 2009. The entire disclosure of each of these applications is hereby incorporated by reference.

The present invention relates to a catalyst system. In particular the invention relates to a catalyst in the form of metal or an alloy that is encapsulated within a polymer shell or matrix. More specifically the invention is directed towards reactive catalytic metals that may be pyrophoric or otherwise reactive in air and/or susceptible to oxidation. In particular, the invention is concerned with catalysts based on nickel.

Raney or sponge nickel is highly hazardous: a self-igniting solid; produces hazardous fumes when burning; causes irritation of the respiratory tract, nasal cavities; causes pulmonary fibrosis if inhaled; ingestion may lead to convulsions and intestinal disorders; causes eye and skin irritation; and chronic exposure may lead to pneumonitis and sensitization ("nickel itch").

The invention provides metal catalysts that avoid such problems and have a good shelf life and working life. Recent European legislation means that new drug products must contain less than 5 parts per million of residual metal catalyst. Hence there is an urgent requirement for cleaner catalyst systems that do not contaminate products or waste streams with metal residues.

Despite the many operational difficulties caused by sponge nickel's hazardous nature, it is still widely used as a catalyst in a variety of organic syntheses. Most commonly it is used for hydrogenation reactions because of its effectiveness at carrying out certain transformations.

Other problems with nickel as a catalyst include the hazardous nature of sponge nickel. This means that the catalyst can present significant safety and handling issues to users. In addition the recently variable nickel prices mean that such catalysts are no longer a reliably cheap option.

Microencapsulated catalyst systems have been described in the prior art.

WO 03/006151 describes encapsulated catalyst systems and methods for their production. In particular, this publication describes palladium-based encapsulated catalysts that find use in coupling reactions. These palladium-based systems are most often derived by micro-encapsulation of palladium acetate.

WO 2005/016510 describes a process in which a metal catalyst is microencapsulated in the presence of a ligand. This publication describes that the use of a ligand may reduce catalyst leaching during the encapsulation process.

WO 2007/096592 discloses a method of preparing a microencapsulated catalyst. This disclosure is particularly concerned with the preparation and use of palladium-based catalysts. In this method, a metal source and a ligand source may be separately encapsulated to produce the active catalytic species in situ. The ligands exemplified are polymeric ligands.

The ultimate catalytic species in this disclosure is a metal-ligand complex or compound.

WO 2005/016510 describes a method for generating porous polymer microspheres which can be used to enclose metal catalysts optionally with an added ligand. The ligand is chosen such that it may interact with the metal catalyst to form a new metal-ligand catalyst species. The microspheres are formed through interfacial polymerisation of a dispersion of monomer and material to be encapsulated in a continuous phase.

U.S. Pat. No. 3,594,666 describes a system for the microencapsulation of heterogeneous catalysts.

The possibility of altering the properties of metal catalysts such as sponge nickel catalysts to facilitate their use has also been discussed in the prior art.

GB 2052296 describes the preparation of a non-pyrophoric Raney catalyst by coating a particulate Raney catalyst in a solid wax. Although this generates a particle coated in a wax, fat or organic polymer which mitigates the pyrophoricity of the material, the coating is not permanent and must be removed to allow reaction. However, until removed, the coating prevents the reaction medium contacting the catalyst. In addition the coating material will then subsequently contaminate the reaction mixture. This contamination may be significant as sponge nickel catalysts are frequently used in high loadings. Catalysts of this type will be unacceptable for pharmaceutical and fine chemistry applications due to the likelihood of significant trace amounts of nickel remaining in the end product and the problem of removing the correspondingly large quantities of wax or coating material.

U.S. Pat. No. 4,895,994 describes a process for generating Raney catalysts in a solid polymer support. The polymer bound catalyst is formed by mixing Raney alloy with high molecular weight polymer and optionally a plasticiser then forming the mixture into shapes by extrusion or cutting. Again the nickel is embedded in the solid polymer and the reaction medium is unable to contact the nickel until it is removed. The catalyst can then be activated by treatment with a sodium hydroxide solution to leave a polymer bound active catalyst. Alternatively the polymer is removed by calcination followed by activation to give a highly specific shaped Raney nickel catalyst.

One problem with the system is that since the polymer is not cross-linked it may be dissolved or softened by certain reaction solvents perhaps prematurely releasing the nickel catalyst into solution. The reactivity may also be limited by the low porosity of the polymer which influences the accessibility to the catalyst. In addition, some of the metal is inevitably present at the surfaces of the shaped catalyst and this increases the risk of leaching of the metal or commencement of the reaction prematurely.

In one approach, commercially available amino coated metal catalysts are provided which are in the form of solid ½ cubes that are non-pyrophoric. These catalysts are activated sponge metal encapsulated catalysts in which water has been displaced by an aliphatic amine. The catalyst powder is released after charging into the desired solvent. Since the sponge metal catalyst is not crossed linked to the coating the amine will be released into solution. The amine coating will then contaminate the reaction mixture once it has been released to expose the metal sponge.

In a related technique not involving Ni catalysts described in WO 2006/007007, polyvinylpyridines are used to coat titanium zeolite catalysts. A suspension of solid zeolite particles are surrounded by a thin layer of polymer either by a coacervation approach or by in-situ interfacial polymerisation around the particles. These catalysts are used for olefin epoxidation.

Each of the various prior art systems has its own set of problems. There is thus a need for a convenient, reliable, safe to handle, economic catalyst system.

Not all reactions are capable of catalysis by transition metal compounds or compounds of other metals. However, the reactivity and/or other handling problems mean that it has not previously been possible to prepare suitable metal catalysts of the type envisaged by the invention. Known catalysts may have particles of various size and shape which may lead to inconsistencies in catalyst behaviour. There are several reasons for this including the difficulty in producing particles having the desired consistent size and morphology of the metal and the fact that metals are not soluble in any conventional reaction medium. This makes it problematic to prepare uniform consistent catalytic materials.

It is an aim of the present invention to provide a convenient and less hazardous catalyst system. The catalyst should be easy to prepare and use. It is a further aim to provide a catalyst system in which the relative amount of metal is reduced. It is a further aim to provide a relatively cheap and economic catalyst. Another aim is to produce a catalyst system which can be used in a number of chemical reactions without resulting in excessive quantities of residual catalyst appearing in the final product. A further aim is to produce a catalyst that can be recovered easily from the reaction. Ideally, the catalyst system will be capable of reuse and/or recycling.

The present invention satisfies some or all of the above aims.

In one aspect, the present invention provides a microencapsulated metal catalyst system, the catalyst system comprising at least one metal and/or at least one metal alloy and a polymeric microsphere which is permeable to liquid, wherein the or each metal and/or metal alloy is retained inside the polymeric microsphere but is in fluid communication with the exterior, and wherein the or each metal and/or metal alloy is not associated with or bound to a ligand. The polymeric material thus forms permeable (to liquid) walls of the microsphere and provides one or more cavities within which the catalytic material is retained.

The metal or metal alloy is preferably not in a catalytically active form when first encapsulated. The metal or metal alloy is activated by reaction of the system with a suitable reagent to form the ultimate catalyst that is employed in the chosen reaction. The reagent used to form the ultimate catalyst may, for example, be an acid or a base. Preferably the activating agent is a base.

The term microencapsulation can be used to refer to processes which lead to products which may have very different properties. A microcapsule is often used to refer to a core-shell system, in which an encapsulated core is surrounded by a thin polymer shell. These systems are often designed such that the shell can be ruptured to allow release of the core material (a fragrance, active compound etc.). The term microsphere as used in the present context to describe the microencapsulated metal catalyst system of the present invention is used to describe a system where a continuous polymer matrix makes up the particle which encases the encapsulated material.

The or each metal and/or metal alloy is not associated with a ligand and is present within the interior of the polymer microsphere in the absence of any ligand provided as part of the catalyst system. The catalytic species is therefore the metal or metals present in oxidation state zero. Where a metal alloy is present and is used as the catalytic species, the component metals are again in oxidation state zero.

The metal or metal alloy may be obtained from a metal precursor. This can be in the form of an alloy mixture. For example, the metal can be Raney nickel. The metal alloy can be a Raney nickel precursor such as an aluminium nickel alloy. The most common metals which are used to prepare sponge metal catalysts are nickel, copper, cobalt and iron. These materials are generally referred to as sponge or skeletal metal catalysts; Raney Nickel is a trademark of W.R. Grace.

Thus in one embodiment, the metal catalyst encapsulated in the microsphere is in the form of a sponge. In an alternative embodiment, the catalyst may be present in the form of discrete particles held within the microsphere.

We now disclose a method for generating microspheres containing solid particles of nickel catalyst alloy. By subsequent activation of the catalyst containing microspheres an active sponge nickel catalyst is produced. The active catalyst is therefore generated in situ. This can be done at the point at which it is ready to be used in a reaction.

One advantage of the catalysts of the present invention is that an encapsulated reactive catalyst such as Raney nickel can be provided in a form which is easier to handle, safer to use and dispose of. This is achieved without contamination of the reaction medium with polymer residues or wax etc. The catalysts of the present invention also overcome the problem of leaching of the metal which is common in many prior art systems.

Thus, in one embodiment of the invention a metal alloy which is used as a metal precursor, for example a nickel aluminium alloy in finely divided form, is encapsulated. This can be achieved using one of the encapsulation procedures described below. Active nickel catalyst can then be produced when required by treating the encapsulated alloy with strong base. This dissolves the aluminium leaving behind nickel in the form of a fine powder catalyst. The nickel is retained wholly within the polymeric matrix which is porous. The solid phase of the polymer does not contain any nickel. In an embodiment, the resulting nickel has a uniform particle distribution throughout the polymeric microsphere.

Nickel alloy is a particularly preferred candidate for encapsulation. Alternatively, in another embodiment, the metal such as nickel or another reactive metal may be prepared in microencapsulated form by encapsulation of a metal compound (i.e. a metal precursor) which can be decomposed easily. This may be by the application of heat, light or other actinic radiation to decompose the metal compound or alloy.

Other suitable catalytic materials are all of those elements of the three "d-block" transition metal series commencing with the elements scandium, ytterbium and lutetium. Preferred elements for forming the ultimate metal or metal alloy catalyst include: cobalt, rhodium, iridium, nickel, palladium, platinum. Nickel, copper, cobalt, iron, palladium and platinum are particularly preferred, and nickel is most preferred.

In another alternative embodiment, the metal is already in its active form and is simply encapsulated. In another embodiment, the metal, metal alloy, or precursor metal compound is deliberately chosen so that the resulting metal has a small particle size range and/or uniform particle size distribution.

A known deactivation pathway of sponge metal catalysts involves the collapse of the highly porous sponge structure. A further advantage of the catalysts of the present invention is that the polymer matrix is able to support the porous metal structure. This may prevent collapse of the porous metal structure and thus reduce the deactivation pathway. The catalysts thus have an extended life relative to known sponge metal catalysts.

The term "microencapsulated" refers to catalyst which is contained within a permeable polymer matrix. This means that the polymer matrix containing the catalyst is itself in the form of a microcapsule, formed for example by one of the techniques described in greater detail below. A microcapsule formed by such techniques will be generally spherical or collapsed spherical and have a mean diameter of from 1 to 1000 microns, preferably from 25 to 500 microns and especially from 50 to 300 microns. The polymer microcapsule matrix is permeable to the extent that the reaction medium being catalysed is capable of contacting the encapsulated catalyst.

Various processes for microencapsulating material are available. These processes can be divided into three broad categories (a) physical, (b) phase separation and (c) interfacial reaction methods. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, the core material is emulsified or dispersed in an immiscible continuous phase, and then an interfacial polymerization reaction is caused to take place at the surface of the core particles thereby forming microcapsules.

We have found that procedures for microencapsulating the metal itself or the metal precursor which have been described in the art for the preparation of metal-ligand catalyst systems can also be used for the preparation of encapsulated metal catalysts according to the present invention. These disclosures of suitable microencapsulation techniques include WO 2003/006151, WO 2005/016510 and WO 2007/096592. These systems form part of the present invention. In the interests of brevity, the content of these disclosures is not reproduced here in full. However, it is specifically intended that the contents of these disclosures insofar as they relate to microencapsulation processes and suitable polymeric materials are to be incorporated herein by reference. In other words, the microencapsulation techniques and materials described in these documents referred to above specifically form part of the disclosure of the present invention for the preparation of encapsulated metal catalysts according to the present invention.

There are various types of interfacial polymerisation techniques but all involve reaction at the interface of a dispersed phase and a continuous phase in an emulsion system. Typically the dispersed phase is an oil phase and the continuous phase is an aqueous phase but interfacial polymerisation reactions at the interface of a continuous oil phase and a dispersed aqueous phase are also possible. Thus for example an oil or organic phase is dispersed into a continuous aqueous phase comprising water and a surface-active agent. The organic phase is dispersed as discrete droplets throughout the aqueous phase by means of emulsification, with an interface between the discrete organic phase droplets and the surrounding continuous aqueous phase solution being formed. Polymerisation at this interface forms the microcapsule shell surrounding the dispersed phase droplets. In one type of interfacial condensation polymerisation microencapsulation process, monomers contained in the oil and aqueous phase respectively are brought together at the oil/water interface where they react by condensation to form the microcapsule wall. In another type of polymerisation reaction, the in situ interfacial condensation polymerisation reaction, all of the wall-forming monomers are contained in the oil phase. In situ condensation of the wall-forming materials and curing of the polymers at the organic-aqueous phase interface may be initiated by heating the emulsion to a temperature of between about 20° C. to about 100° C. and optionally adjusting the pH. The heating occurs for a sufficient period of time to allow substantial completion of in situ condensation of the prepolymers to convert the organic droplets to capsules consisting of a solid permeable polymer matrix entrapping the organic core materials.

One type of microcapsule prepared by in situ condensation and known in the art is exemplified in U.S. Pat. No. 4,956,129 and U.S. Pat. No. 5,332,584. This disclosure also forms part of the invention insofar as it relates to encapsulation processes. These microcapsules, commonly termed "aminoplast" microcapsules, are prepared by the self-condensation and/or cross-linking of etherified urea-formaldehyde resins or prepolymers in which from about 50 to about 98% of the methylol groups have been etherified with a $C_4$-$C_{10}$ alcohol (preferably n-butanol). The prepolymer is added to or included in the organic phase of an oil/water emulsion. Self-condensation of the prepolymer takes place optionally under the action of heat at low pH. To form the microcapsules, the temperature of the two-phase emulsion is raised to a value of from about 20° C. to about 90° C., preferably from about 40° C. to about 90° C., most preferably from about 40° C. to about 60° C. Depending on the system, the pH value may be adjusted to an appropriate level. For the purpose of this invention a pH of about 1.5 to 3 is appropriate.

As described in U.S. Pat. No. 4,285,720 (also incorporated by reference as part of the present invention) the prepolymers most suitable for use in this invention are partially etherified urea-formaldehyde prepolymers with a high degree of solubility in organic phase and a low solubility in water. Etherified urea-formaldehyde prepolymers are commercially available in alcohol or in a mixture of alcohol and xylene. Examples of preferred commercially available prepolymers include the Beetle etherified urea resins manufactured by BIP (eg BE607, BE610, BE660, BE676) or the Dynomin N-butylated urea resins from Dyno Cyanamid (eg Dynomin UB-24-BX, UB-90-BX etc).

Acid polymerisation catalysts capable of enhancing the microcapsule formation can be placed in either the aqueous or the organic phase. Acid polymerisation catalysts are generally used when the core material is too hydrophobic, since they serve to attract protons towards the organic phase. Any water soluble acid polymerisation catalyst which has a high affinity for the organic phase can be used. Carboxylic and sulphonic acids are particularly useful.

One further type of microcapsule prepared by in situ condensation and found in the art, as exemplified in U.S. Pat. No. 4,285,720 (also incorporated by reference as part of the present invention) is a polyurea microcapsule which involves the use of at least one polyisocyanate such as polymethylene polyphenyleneisocyanate (PMPPI) and/or tolylene diisocyanate (TDI) as the wall-forming material. In the creation of polyurea microcapsules, the wall-forming reaction is generally initiated by heating the emulsion to an elevated temperature at which point a proportion of the isocyanate groups are hydrolyzed at the interface to form amines, which in turn react with unhydrolyzed isocyanate groups to form the polyurea microcapsule wall. During the hydrolysis of the isocyanate monomer, carbon dioxide is liberated. The addition of no other reactant is required once the dispersion establishing droplets of the organic phase within a continuous liquid phase, i.e. aqueous phase, has been accomplished. Thereafter, and preferably with moderate agitation of the dispersion, the formation of the polyurea microcapsule can be brought about by heating the continuous liquid phase or by introducing a polymerisation catalyst such as an alkyl tin or a tertiary amine capable of increasing the rate of isocyanate hydrolysis.

The amount of the organic phase may vary from about 1% to about 75% by volume of the aqueous phase present in the reaction vessel. The preferred amount of organic phase is about 10 percent to about 50 percent by volume. The organic polyisocyanates used in this process includes both aromatic and aliphatic mono and poly functional isocyanates. Examples of suitable aromatic diisocyanates and other polyisocyanates include the following: 1-chloro-2,4-phenylene diisocyanate, m-phenylene diisocyanate (and its hydrogenated derivative), p-phenylene diisocyanate (and its hydrogenated derivative), 4,4'-methylenebis (phenyl isocyanate), 2,4-tolylene diisocyanate, tolylene diisocyanate (60% 2,4-isomer, 40% 2,6-isomer), 2,6-tolylene diisocyanate, 3,3'-dimethyl-4,4'-biphenylene diisocyanate, 4,4'-methylenebis (2-methylphenyl isocyanate), 3,3'-dimethoxy-4,4'-biphenylene diisocyanate, 2,2',5,5'-tetramethyl-4,4'-biphenylene diisocyanate, 80% 2,4- and 20% 2,6-isomer of tolylene diisocyanate, polymethylene polyphenylisocyante (PMPPI), 1,6-hexamethylene diisocyanate, isophorone diisocyanate, tetramethylxylene diisocyanate and 1,5-naphthylene diisocyanate, hydrophilic aliphatic polyisocyanates based on hexamethylene diisocyanate (eg Bayhydur 3100, Bayhydur VP LS2319 and Bayhydur VP LS2336) and hydrophilic aliphatic polyisocyanates based on isophorone diisocyanate (eg Bayhydur VP LS2150/1).

It may be desirable to use combinations of the above mentioned polyisocyanates. Preferred polyisocyanates are polymethylene polyphenylisocyanate (PMPPI) and mixtures of polymethylene polyphenylisocyanate (PMPPI) with tolylene diisocyanate or other difunctional aromatic or aliphatic isocyanates.

One further class of polymer precursors consists of a primarily oil-soluble component and a primarily water-soluble component which react together to undergo interfacial polymerisation at a water/oil interface. Typical of such precursors are an oil-soluble isocyanate such as those listed above and a water-soluble poly amine such as ethylenediamine and/or diethylenetriamine to ensure that chain extension and/or cross-linking takes place. Cross-linking variation may be achieved by increasing the functionality of the amine. Thus for example, cross-linking is increased if ethylenediamine is replaced by a polyfunctional amine such as DETA (Diethylene triamine), TEPA (Tetraethylene pentamine) and other well established cross linking amines. Isocyanate functionality can be altered (and thus cross-linking also altered) by moving from monomeric isocyanates such as toluene diisocyanate to PMPPI. Mixtures of isocyanates, for example mixtures of tolylene diisocyanate and PMPPI, may also be used. Moreover, the chemistry may be varied from aromatic isocyanates to aliphatic isocyanates such as hexamethylenediisocyanate and isophorone diisocyanate. Further modifications can be achieved by partially reacting the (poly) isocyanate with a polyol to produce an amount of a polyurethane within the isocyanate chemistry to induce different properties to the wall chemistry. For example, suitable polyols could include simple low molecular weight aliphatic di, tri or tetraols or polymeric polyols. The polymeric polyols may be members of any class of polymeric polyols, for example: polyether, polyTHF, polycarbonates, polyesters and polyesteramides. One skilled in the art will be aware of many other chemistries available for the production of a polymeric wall about an emulsion droplet. As well as the established isocyanate/amine reaction to produce a polyurea wall chemistry, there can be employed improvements to this technology including for example that in which hydrolysis of the isocyanate is allowed to occur to an amine which can then further react internally to produce the polyurea chemistry (as described for example in U.S. Pat. No. 4,285,720). Variation in the degree of cross linking may be achieved by altering the ratio of monomeric isocyanate to polymeric isocyanate. As with the conventional isocyanate technology described above, any alternative isocyanates can be employed in this embodiment.

One skilled in the art will be aware that the various methods previously described to produce polyurea microcapsules typically leave unreacted amine (normally aromatic amine) groups attached to the polymer matrix. In some cases it may be advantageous to convert such amine groups to a substantially inert functionality. Preferred are methods for the conversion of such amine groups to urea, amide or urethane groups by post reaction of the microcapsules in an organic solvent with a monoisocyanate, acid chloride or chloroformate respectively.

U.S. Pat. No. 6,020,066 (assigned to Bayer AG) discloses another process for forming microcapsules having walls of polyureas and polyiminoureas, wherein the walls are characterized in that they consist of reaction products of crosslinking agents containing $NH_2$ groups with isocyanates. The crosslinking agents necessary for wall formation include di- or polyamines, diols, polyols, polyfunctional amino alcohols, guanidine, guanidine salts, and compounds derived there from. These agents are capable of reacting with the isocyanate groups at the phase interface in order to form the wall.

The preferred materials for the microcapsule are a polyurea, formed as described in U.S. Pat. No. 4,285,720, and a urea-formaldehyde polymer as described in U.S. Pat. No. 4,956,129. Again, the teachings of these documents in so far as they relate to materials suitable for forming microcapsules. Polyurea is preferred because the microcapsule is formed under very mild conditions and does not require acidic pH to promote polymerisation and so is suitable for use when encapsulating acid-sensitive catalysts. The most preferred polymer type for the microcapsule is polyurea as described in U.S. Pat. No. 4,285,720 based on the PMPPI polyisocyanate either alone or in combination with other aromatic di or multi functional isocyanates.

Microencapsulation techniques described above most commonly involve the microencapsulation of an oil phase dispersed within an aqueous continuous phase, and for such systems the catalyst is suitably capable of being suspended within the microencapsulated oil phase or more preferably is soluble in a water-immiscible organic solvent suitable for use as the dispersed phase in microencapsulation techniques. The scope of the present invention is not however restricted to the use of oil-in-water microencapsulation systems and water-soluble catalysts may be encapsulated via interfacial microencapsulation of water-in-oil emulsion systems. Water-soluble catalysts may also be encapsulated via interfacial microencapsulation of water-in-oil-in-water emulsion systems.

Preferably the metal catalyst, solvent and wall forming material are dispersed as a single organic phase into the continuous aqueous phase.

The loading level of the microencapsulated catalyst can be varied. Microencapsulated catalysts with loadings 0.01 mmol/g to 0.8 mmol/g are typical, where the loading is based on metal content. Loadings of 0.2 mmol/g to 0.6 mmol/g are preferred. In this invention loadings of the microencapsulated metal or metal alloy are considerably higher ranging from 1 wt % to 40 wt %, where loading is based on the mass of metal to mass of microcapsule. Loadings of 5 wt % to 30 wt % are preferred.

Typical examples of surfactants which can be used to facilitate formation of the emulsion include:
a) condensates of alkyl (eg octyl, nonyl or polyaryl) phenols with ethylene oxide and optionally propylene oxide and anionic derivatives thereof such as the corresponding ether sulphates, ether carboxylates and phosphate esters;

block copolymers of polyethylene oxide and polypropylene oxide such as the series of surfactants commercially available under the trademark PLURONIC (PLURONIC is a trademark of BASF);

b) TWEEN surfactants, a series of emulsifiers comprising a range of sorbitan esters condensed with various molar proportions of ethylene oxide;

c) condensates of $C_8$ to $C_{30}$ alkanols with from 2 to 80 molar proportions of ethylene oxide and optionally propylene oxide; and d) polyvinyl alcohols, including the carboxylated and sulphonated products.

In addition the aqueous phase may contain other additives which may act as aids to the process of dispersion or the reaction process. For example, de-foamers may be added to lessen foam build up, especially foaming due to gas evolution.

A wide variety of materials suitable for use as the oil phase will occur to one skilled in the art. Examples include, diesel oil, isoparaffin, aromatic solvents, particularly alkyl substituted benzenes such as toluene, xylene or propyl benzene fractions, and mixed napthalene and alkyl napthalene fractions; mineral oils, white oil, castor oil, sunflower oil, kerosene, dialkyl amides of fatty acids, particularly the dimethyl amides of fatty acids such as caprylic acid; chlorinated aliphatic and aromatic hydrocarbons such as 1,1,1-trichloroethane and chlorobenzene; esters of glycol derivatives, such as the acetate of the n-butyl, ethyl, or methyl ether of diethylene glycol; the acetate of the methyl ether of dipropylene glycol; ketones such as methyl ethyl ketone, methyl isobutyl ketone, isophorone and trimethylcyclohexanone (dihydroisophorone); ethers such as methyl tert-butyl ether and cyclopentyl methyl ether and the acetate products such as ethyl, hexyl, or heptyl acetate. Organic liquids conventionally preferred for use in microencapsulation processes are xylene, diesel oil, isoparaffins and alkyl substituted benzenes.

In addition to the catalyst or catalyst precursor, the oil phase may also include non-ligating dispersing agents to aid the homogeneous distribution of the particulate material through the oil phase. Typical examples include Solsperse 32000 and EFKA-4401.

The microcapsule wall-forming material may for example be a monomer, oligomer or pre-polymer and the polymerisation may take place in situ by polymerisation and/or curing of the wall-forming material at the interface. In the alternative polymerisation may take place at the interface by the bringing together of a first wall-forming material added through the continuous phase and a second wall-forming material in the discontinuous phase.

Surprisingly, we have also found that despite the absence of ligands on the metal or associated with the metal inside the polymer matrix, which ordinarily interact with the polymer matrix to prevent leaching of the metal catalyst, the metal can still be retained within the microsphere, i.e. remain microencapsulated during and after completion of the reaction. Thus, little or no loss of the metal during reaction can be achieved using the catalysts of the invention. This is contrary to expectations since it is believed that there is no chemical bond between the nickel and the polymeric microsphere. This is a significant performance benefit, particularly when catalysing reactions intended to produce active drugs or intermediates for active drugs. Reactions catalysed by the invention are thus capable of meeting the current strict targets for levels of metal impurities in final drug products.

Without wishing to be bound by theory, it is normally believed that polymeric ligands are bound tightly within the polymer matrix of the microcapsule, thereby retaining the catalyst within the microcapsule. This binding may arise through steric interactions (such as chain entanglement or greatly reduced diffusion rates of larger molecules) or through chemical binding, such as ionic, electrostatic or covalent bonds formed by polymerisation with the microcapsule shell or a constituent (e.g. a monomer or prepolymer) thereof. Such interactions are absent in the catalysts of the present invention. Nevertheless, the finely divided metal is retained within the void defined by the polymeric matrix. The metal particles thus do not contaminate reaction products as conventional catalysts.

Surprisingly we have also found that the polyurea matrix of the microspheres is sufficiently resistant to the strong basic conditions used during activation of the encapsulated alloy to form the metal or metal alloy that functions as the catalyst in the chosen reaction. Furthermore, we have found that the microspheres retain their structural integrity following both the activation procedure and following the use of the activated encapsulated catalyst particles in chemical transformations. The lifetime is thus extended relative to known catalysts.

A further technical benefit of the catalysts is that they can be recovered and reused (after suitable washing) in subsequent reactions. At end of life, the metal can then be recovered and recycled. This is a significant advantage over prior art catalysts.

A further benefit is the improved safety profile of the catalysts. Preliminary hazard studies have indicated no evidence of pyrophoricity. This is a significant advantage over conventional catalysts and allows for safer storage, handling, recovery and disposal.

In some instances, the metal catalyst being encapsulated may increase the rate of the interfacial polymerisation reactions. In such cases it may be advantageous to cool one or both of the organic and continuous aqueous phases such that interfacial polymerisation is largely prevented whilst the organic phase is being dispersed. The reaction is then initiated by warming in a controlled manner once the required organic droplet size has been achieved. For example, in certain reactions the aqueous phase may be cooled to less than 10° C., typically to between 5° C. to 10° C., prior to addition of the oil phase and then when the organic phase is dispersed the aqueous phase may be heated to raise the temperature above 15° C. to initiate polymerisation.

According to a further aspect of the present invention there is provided a process for the preparation of a microencapsulated catalyst which comprises forming a matrix microsphere by interfacial polymerisation in the presence of a metal, a metal alloy or a metal precursor. The encapsulated catalyst formed in this process is a catalyst as described above.

A process of the invention may therefore comprise the steps:

(a) dispersing at least one metal and/or metal alloys in a first phase optionally in the presence of dispersing agents but without the presence of any bound or unbound ligand, (b) dispersing the first phase in a second, continuous phase to form an emulsion, (c) reacting one or more microcapsule wall-forming materials at the interface between the dispersed first phase and the continuous second phase to form a microcapsule polymer shell encapsulating the dispersed first phase core, and optionally (d) recovering the microcapsules from the continuous phase.

Another significant benefit of the catalysts of the present invention resides in the uniformity of the metal particle sizes produced on activation of the metal catalyst such as nickel. As the metal particles are physically entrapped within a polymer matrix they are unable to aggregate, coalesce or sinter to form larger particles, a process which can occur with conventional sponge nickel catalysts. This means that the catalyst behaves in a consistent and predictable manner.

Reactions performed using catalysts of the invention are expected to proceed at more uniform rates. Similarly, the exotherms generated during reactions is more controlled. This is particularly important for reactions conducted on an industrial scale. The advantages of an encapsulated nickel catalyst having a carefully controlled particle size profile have not previously been recognised in the art. The catalysts of the invention are useful in a wide variety of reactions, particularly in the production of pharmaceutical actives and intermediates. Recent European legislation means that new drug products must contain less than 5 parts per million of residual metal catalyst. Similarly, the FDA impose strict requirements on the levels of residual metals in active drug products. Hence, the catalysts of the invention provide a cleaner catalyst system, relative to known catalysts, that does not contaminate products or waste streams with metal residues.

A summary of an encapsulated nickel catalyst according to the invention and its method of preparation is now described below. For ease of reference, the catalyst is referred to below as Ni EnCat.

General Procedures

GCMS analysis was carried out using a Varian Saturn 2100T GC/MS instrument with a FactorFour VF-5MS 30 m×0.25 mm capillary column. Identification and quantification of the products were determined by GCMS analysis and relative yields were based on peak area ratio.

HPLC was carried out using a Waters Alliance 2695 LC system with UV detection at 190 to 400 nm.

ICP analysis of product metal content was carried out using a Thermo-Jarrell-Ash Atom Scan 16 measuring unknown samples against calibration carried out using standards of known concentration.

General Encapsulation Method

A dispersant was dissolved in an organic phase such as chloroform at a loading of 1-20 wt % based on the target quantity of metal alloy to be encapsulated. A metal or metal alloy was added at a loading of 1-40 wt % of the target polymer content of the microspheres. The suspension was stirred for 10-30 minutes. Polyfunctional isocyanate was added to the suspension at the desired amount to generate the required porosity in the product, typically a polymer content of 30% in the final EnCat bead.

An aqueous phase consisting of stabilisers/surfactants was prepared separately. This was stirred at high shear and the oil phase added over a few minutes. The shear rate was subsequently reduced and the microspheres left to cure at room temperature for several hours followed by at least one hour at 45° C. The aqueous phase was decanted and the beads washed with water by decanting twice. The encapsulated metal or metal alloy were collected by filtration and stored water wet.

EXAMPLE 1

Nickel-Aluminium Alloy Encapsulation at 1 Kg Scale

The following raw materials are required for a notional 1.33 kg batch, which gives approx 2.8 kgs beads @ 50% water-wet:

| Material | Form | Weight | Volume |
|---|---|---|---|
| Stabiliser Reax ™ 100M | Solid | 840 g | n/a |
| Surfactant Tergitol ™ XD as 100% | Solid | 105 g | n/a |
| Surfactant Polyvinyl alcohol as 100% | Solid | 420 g | n/a |
| Deionised Water for aqueous phase | Liquid | n/a | 9135 ml |
| Chloroform, stabilised with amylene | Liquid | 2880 g | 2009 ml |
| Polymethylpolyphenyl isocyanate | Liquid | 1350 g | 1125 ml |
| Dispersant Solsperse ™ 32000 | Solid | 27.34 g | n/a |
| Nickel-Aluminum Alloy | Solid | 270 g | n/a |
| Deionised Water for Decantation | Liquid | 20000 g | 20000 ml |
| Deionised Water for washes | Liquid | 50000 g | 50000 ml |
| Organic Base | Solid | 13.5 g | n/a |
| Industrial Methylated Spirit (IMS) | Liquid | 86000 g | 20000 ml |

A. Preparation of Aqueous Phase in Reactor 1

In a 20 L reactor fitted with mechanical stirrer, thermocouple, condenser and feed line 1.68 L of deionised water was added followed by 420 g of Surfactant polyvinyl alcohol and 105 g of Surfactant Tergitol™ XD. The contents of the reactor were then heated to 60-65° C. and agitated until all solids are dissolved. The reactor contents were then cooled to 28° C. and Stabiliser Reax™ 100M was added to the reactor. 7.45 L deionised water was then added to the reactor and agitated until all solids are dissolved.

B. Preparation of Organic Phase in Reactor 2

A 5 L feed reactor was purged with nitrogen and then 532 ml chloroform was added to the reactor. The dispersant, Solsperse™ 32000 in chloroform solution (27.34 g in 70 mls Chloroform), was then added to the reactor followed by 389 ml chloroform and the contents stirred for 10 minutes. The Nickel-Aluminium alloy (270 g) was then added to the reactor followed by 468 ml chloroform and the contents stirred for 50 minutes at approximately 25° C. 1350 g of polymethylpolyphenyl isocyanate (PMPPI) was added to the reactor followed by the remaining 520 ml chloroform. The dark grey mixture was then agitated for 50 minutes at 25° C.

C. Droplet Formation

The agitation speed in main reactor was set to "high speed" setting and the temperature control for the reactor was set to 28° C.

The oil phase was transferred into the aqueous phase at a constant flow over 2-4 minutes via a peristaltic pump fitted with solvent resistant versinic rubber tubing. The reactor agitator was maintained at the "high speed" for a further 3.5 minutes then reduced to "low speed". A representative sample of the agitated reactor contents was taken, and visually examined using a microscope for acceptable droplet size. If droplets appear to be too large, the reactor agitation can be increased to "high speed" for a further 5 minutes, then adjusted to "low speed", and visual test repeated.

D. Bead Curing 13 g of Organic Base was added to the reactor whilst agitation was maintained at "low speed". Antifoam was added in small quantities during the process, as required to minimise foaming. The temperature was maintained at 28° C. for 0.66 hours and then the contents slowly heated over a minimum of 4 hours, to 40° C. by addition of heat to the jacket. Care was taken not to heat too quickly, or to have a high temperature differential between jacket and reactor contents, to minimise the likelihood of significant foaming. If vigorous foaming started before 40° C. is reached, the reactor temperature was held at current temperature until the foaming subsided, then gentle heating was resumed. The batch was held at 40° C. until foaming subsided for 1 hour. 1.5 L deionised water was then added to the reactor and the contents cooled to 25° C. over 1 hour and held at 25° C. for up to 18 hours, or until foaming had largely subsided. A sample of the beads was taken and tested for mechanical strength. The agitation was reduced by 66%, and approx 3 L was decanted from the upper layer. A further 3 L deionised water was added to the reactor.

E. Aqueous Decantation and Fines Removal

The agitator was stopped and most of the aqueous layer was decanted using a vacuum lance, fitted with a 100 micron filter on the end, without disturbing the bulk of the beads. A further 3 L deionised water was added to the reactor and the decanting process repeated four times.

F. Bead Washing

The reaction product was transferred to a sintered filtration unit and residual aqueous phase removed by applying vacuum to the sealed system. 10 L of deionised water was then added to the beads and the mixture agitated slowly for 10 minutes. The filtrate was then removed and this process was repeated 3 times.

10 L of IMS was then added to wash the beads and this was repeated once more. Finally the product was washed with 10 L of deionised water twice and the contents filtered until material was 50% water wet. The beads were discharged from the filtration system and stored as water wet beads.

General Activation Method

Activation of the catalyst was achieved by heating the beads in a 6 M solution of sodium hydroxide at 90° C. for 1-5 hours. The solution was cooled, removed and replaced by a further portion of 6 M sodium hydroxide. The mixture was heated for a further 1 hour, then the solution removed and the beads washed with water until pH<9 is reached (approximately 10 washes). The active catalyst beads were stored under nitrogen degassed water.

EXAMPLE 2

Preparation of Activated Ni EnCat at 250 g Scale

In a 2 L screw-cap jar, 1 L deionised water was added followed by 240 g sodium hydroxide pellets in 50 g aliquot at 5 minute intervals whilst stirring. Once all the sodium hydroxide was added the solution was allowed to cool to room temperature and continuously sparged with nitrogen.

In a 3 L jacketed-flange reactor fitted with mechanical stirrer, thermocouple, condenser and $N_2$ inlet 400 ml of caustic solution prepared above were added and the reactor sparged with nitrogen. 200 g of wetted Ni EnCat beads were weighed out and added to the reactor in 50 g portions whilst stirring. Rapid effervescence was observed followed by evolution of hydrogen gas which was vented out through a water trap. After 10 minutes the reaction subsided and further 50 g of beads added to the reactor. This process was repeated until all the beads were added to the reactor. The reactor temperature was then gradually increased to 90° C. and held at this temperature for 2 hours. The reactor contents were then cooled to below 35° C. and the caustic layer decanted via a vacuum lance fitted with a 100 micron filter on the end until most of the liquid was removed. 400 ml of 'fresh' caustic solution was then added to the reactor and the contents heated to 90° C. for further 1 hour. After the contents of reactor had cooled to below 35° C., the liquid phase was decanted off and 1 L nitrogen-sparged deionised water added to the reactor and contents agitated.

The stirrer was then stopped and the water layer decanted via the vacuum lance. This process was repeated a further 9 times or until the pH of the water layer was below 9. The beads were then collected and stored under water.

The activity of the Ni EnCat beads produced according to the invention is exemplified by a number of chemical transformations which are conventionally carried out with sponge nickel.

EXAMPLE 3

Reduction of 4-chloronitrobenzene

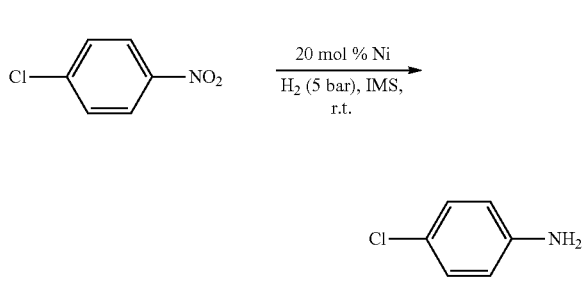

Activated Ni EnCat (0.26 g, water wet, 20 mol % Ni on substrate) was washed with IMS three times to remove water and added to 4-chloronitrobenzene (0.157 g, 1 mmol) dissolved in IMS (4 ml) in a pressure vessel. The vessel was sealed and purged twice with hydrogen then pressurised to 5-6 bar with hydrogen and the contents magnetically stirred at room temperature. Progress of reaction was carried out by GCMS analysis. After 24 h the hydrogen was vented and the Ni EnCat beads removed by filtration. The filtrate was concentrated on a rotary evaporator to give 4-chloroaniline (0.12 g, 95%). GCMS purity 86%.

EXAMPLE 4

Reduction of 4-chlorobenzonitrile

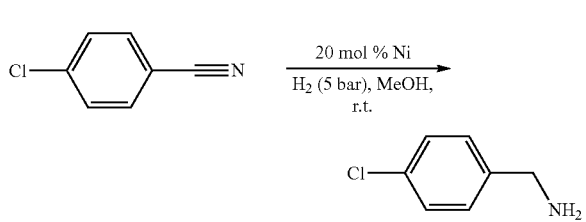

Activated Ni EnCat (0.26 g, water wet, 20 mol % Ni on substrate) was washed with MeOH three times to remove water and added to 4-chlorobenzonitrile (0.137 g, 1 mmol) dissolved in 7 N ammonia in MeOH (4 ml) in a pressure vessel. The vessel was sealed and purged twice with hydrogen then pressurised to 5-6 bar with hydrogen and the contents magnetically stirred at room temperature. Progress of reaction was carried out by GCMS analysis. After 24 h the hydrogen was vented and the Ni EnCat beads removed by filtration. The filtrate was concentrated on a rotary evaporator to give 4-chlorobenzylamine (0.13 g, 91%). GCMS purity 77%.

EXAMPLE 5

Reduction of tert-butyl (((4R,6R)-6-(cyanomethyl)-2,2-dimethyl-1,3-dioxane-4-yl)acetate (1)

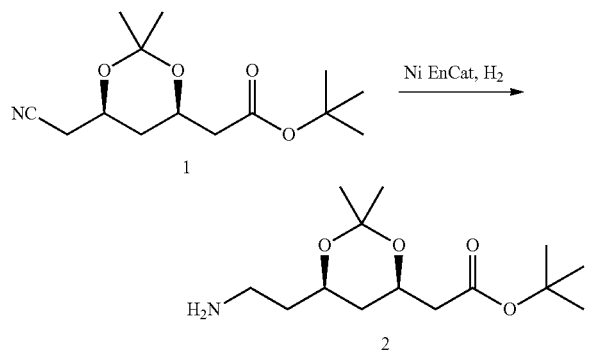

Activated Ni EnCat (0.54 g, water wet, 12.5 wt % Ni on substrate) was washed with MeOH then added to tert-butyl (((4R,6R)-6-(cyanomethyl)-2,2-dimethyl-1,3-dioxane-4-yl) acetate (1) (0.23 g, 0.85 mmol) in toluene (3 ml) and 7 N ammonia in MeOH (1 ml) in a pressure vessel. The vessel was sealed and purged twice with hydrogen then pressurised to 5 bar with hydrogen gas and stirred vigorously at room temperature. Reaction progress was analysed by HPLC. After 24 h the beads were removed by filtration and the reaction mixture concentrated on a rotary evaporator to give tert-butyl (((4R,6R)-6-(2-aminoethyl)-2,2-dimethyl-1,3-dioxane-4-yl) acetate (2) (0.195 g, 85%). Purity by HPLC>95%.

EXAMPLE 6

Reduction of Benzalacetone

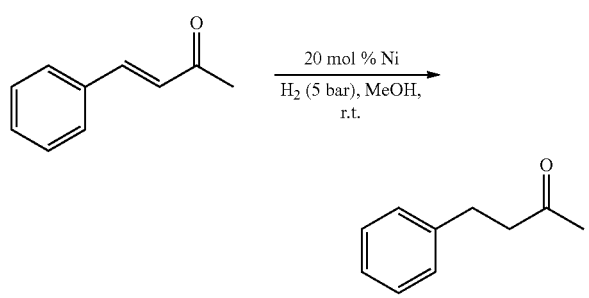

Activated Ni EnCat (0.26 g, water wet, 20 mol % Ni on substrate) was washed with MeOH three times to remove water and added to benzalacetone (0.148 g, 1 mmol) dissolved in MeOH (4 ml) in a pressure vessel. The vessel was sealed and purged twice with hydrogen then pressurised to 5-6 bar with hydrogen and the contents magnetically stirred at room temperature. Progress of reaction was carried out by GCMS analysis. After 24 h the hydrogen was vented and the Ni EnCat beads removed by filtration. The filtrate was concentrated on a rotary evaporator to give 4-phenylbutanone (0.149 g, 99%).

EXAMPLE 7

Optimisation of the hydrogenation of a 4-chloro-2-nitroaromatic 3

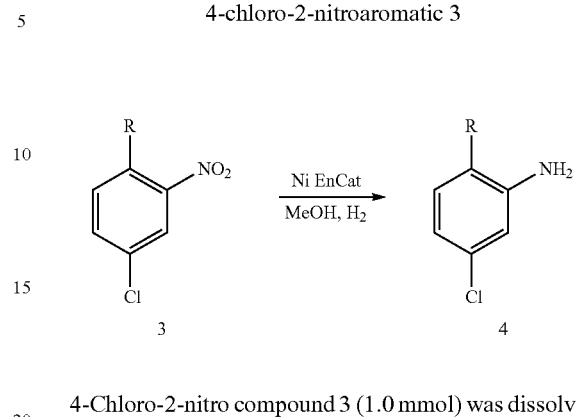

4-Chloro-2-nitro compound 3 (1.0 mmol) was dissolved in methanol (5 mL), glacial acetic acid (1.0 mmol) and Ni EnCat (5-20 mol %) were added, the mixture was purged with $H_2$ and left to stir under 1 bar of $H_2$ for 240 mins at room temperature. Conversion to compound 4 was followed by HPLC.

The reaction was carried out using a range of Ni EnCat catalyst loadings showing that the catalyst charge could be reduced (Table 1).

TABLE 1

| Entry | Catalyst (mol %) | Time (mins) | % Conversion |
|---|---|---|---|
| 1 | NiEnCat ™ (20) | 240 | 100 |
| 2 | NiEnCat ™ (10) | 240 | 100 |
| 3 | NiEnCat ™ (5) | 240 | 100 |

The reactions showed that it was possible to lower the loading of Ni EnCat needed for the reaction to go to completion.

The recyclability of the Ni EnCat in the process was investigated using 5 mol % of the catalyst. 4-Chloro-2-nitro compound 3 (1.0 mmol) was dissolved in methanol (5 mL), glacial acetic acid (1.0 mmol) and Ni EnCat (5 mol %) were added, the mixture was purged with $H_2$ and left to stir under 1 bar of $H_2$ for 240 mins at room temperature. Conversion to compound 4 was followed by HPLC. Once the reaction was complete, the catalyst was allowed to settle and the reaction mixture was removed from the catalyst by decantation. The catalyst bed was washed with methanol (3×5 ml) and then fresh 4-chloro-2-nitro compound 3 (1.0 mmol), glacial acetic acid (1.0 mmol) and methanol (5 mL) were added. The mixture was purged with $H_2$ and left to stir under 1 bar of $H_2$ for 240 mins at room temperature. Conversion to compound 4 was followed by HPLC which again showed complete reaction demonstrating reuse was possible (Table 2).

TABLE 2

| Cycle | Time (mins) | % Conversion |
|---|---|---|
| 1 | 240 | 100 |
| 2 | 240 | 100 |

COMPARATIVE EXAMPLE 1

Activation of Ni/Al Alloy without Encapsulation

For comparison, sponge nickel was prepared by sodium hydroxide activation of the same Ni/Al alloy encapsulated in Ni EnCat. Ni/Al alloy (Aldrich aluminium-nickel catalyst, 0.5 g) was added in small portions to 6 M sodium hydroxide solution (6 ml) at room temperature with stirring. After complete addition of the alloy the solution was heated at 90° C. for 1 h. The solution was cooled, removed and replaced by a further portion of 6 M sodium hydroxide. The mixture was heated for a further 1 h, then the solution removed and the beads washed with water until pH<9 is reached (approximately 10 washes). The active catalyst was stored under nitrogen degassed water.

COMPARATIVE EXAMPLE 2

Sponge Nickel reduction of tert-butyl (((4R,6R)-6-(cyanomethyl)-2,2-dimethyl-1,3-dioxane-4-yl)acetate (1)

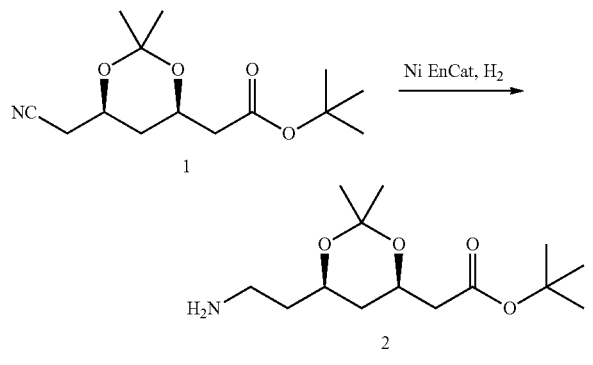

Sponge nickel from Comparative Example 1 (17 mg, 12.5 wt % Ni on substrate) was washed with MeOH then added to tert-butyl (((4R,6R)-6-(cyanomethyl)-2,2-dimethyl-1,3-dioxane-4-yl)acetate (1) (0.23 g, 0.85 mmol) in toluene (3 ml) and 7 N ammonia in MeOH (1 ml) in a pressure vessel. The vessel was sealed and purged twice with hydrogen then pressurised to 5 bar with hydrogen gas and stirred vigorously at room temperature. Reaction progress was analysed by HPLC. After 24 h the catalyst was removed by filtration and the reaction mixture concentrated on a rotary evaporator to give at mixture of tert-butyl (((4R,6R)-6-(2-aminoethyl)-2,2-dimethyl-1,3-dioxane-4-yl)acetate (2) and starting material. Purity by HPLC 53%.

COMPARATIVE EXAMPLE 3

Reduction of 4-chlorobenzonitrile with Sponge Nickel

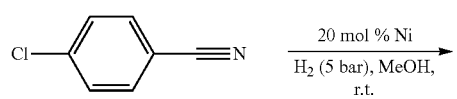

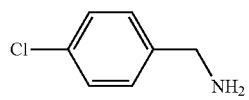

Sponge nickel from Comparative Example 1 (12 mg, 20 mol % Ni on substrate) was washed with MeOH three times to remove water and added to 4-chlorobenzonitrile (0.137 g, 1 mmol) dissolved in 7 N ammonia in MeOH (4 ml) in a pressure vessel. The vessel was sealed and purged twice with hydrogen then pressurised to 5-6 bar with hydrogen and the contents magnetically stirred at room temperature. Progress of reaction was carried out by GCMS analysis. After 24 h the hydrogen was vented and the Ni catalyst removed by filtration. The filtrate was concentrated on a rotary evaporator to give 4-chlorobenzylamine (0.14 g, 99%). GCMS purity 78%.

EXAMPLE 8

Reuse of Ni EnCat and Metal Leaching

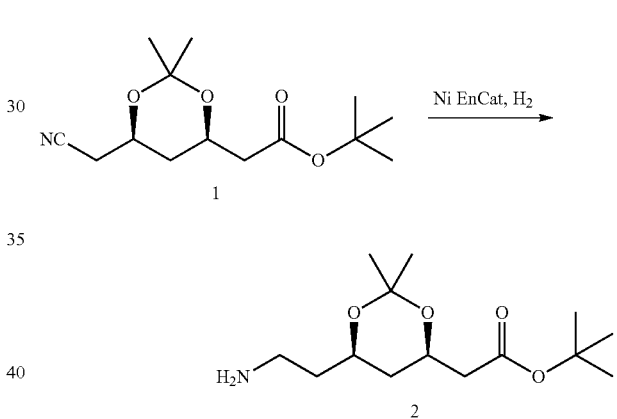

Ni EnCat (1.0 g of 66% water wet beads, 6.5 wt % Ni) was weighed into a glass reaction tube and washed three times with methanol. 1 (0.50 g, 1.86 mmol), methanol (4 ml), conc. ammonia aq. (0.1 ml) and a magnetic stirrer bar were added and the reaction tube sealed in a pressure vessel. The vessel was purged with hydrogen twice then stirred at 45° C. for 16-20 h under 5 bar hydrogen pressure. Reaction mixture was removed from the catalyst by decantation, washing the catalyst residue twice with methanol. Combined methanol washings were concentrated under reduced pressure to yield 2 (0.467 g, 95%). The reaction was analysed by GC-MS which showed a conversion to product of >99%.

Ni content was measured by ICP by dissolving the product in a known mass of DMSO. The unknown was compared against Ni standards of known concentration, taking an average of three measurement. The measured Ni content in the solid was 39 ppm.

At the end of the experiment, the reaction mixture was decanted from the catalyst beads which were then washed three times with methanol before addition of a fresh portion of substrate. This was repeated twice to demonstrate the potential for catalyst recycle (Table 3).

TABLE 3

Ni EnCat Recycling in Hydrogenation of 1 at 45° C.

| Run | Ni loading | Conversions 1 | Conversions 2 | Isolated Yield | Ni content |
|---|---|---|---|---|---|
| 1 | 6.5 | — | 100% | 0.467 g | 39 ppm |
| 2 | 6.5 | <1% | >99% | 0.513 g | 14 ppm |
| 3 | 6.5 | 9% | 91% | 0.512 g | 17 ppm |

The activity of Ni EnCat is maintained in the second run though there is a slight drop off to the third run. Conversions were nonetheless greater than 90% and consistently high isolated yield were maintained throughout. Consistently low levels of Ni were measured in the product.

This example demonstrates that the catalytic system can be reused. The catalysts of the present invention thus exhibit the potential to be re-used in a large number of cycles of the reaction, e.g., more than 10 cycles of the reaction.

COMPARATIVE EXAMPLE 4

Metal Leaching from Sponge Nickel

Nickel catalyst (Sigma-Aldrich Raney® 2400 Nickel, 0.5 g of 50% water wet catalyst, 50 wt % Ni) was weighed into a glass reaction tube and washed three times with methanol. 1 (0.50 g, 1.86 mmol), methanol (4 ml), conc. ammonia aq. (0.1 ml) and a magnetic stirrer bar were added and the reaction tube sealed in a pressure vessel. The vessel was purged with hydrogen twice then stirred at 45° C. for 16-20 h under 5 bar hydrogen pressure. Reaction mixture was removed from the catalyst by decantation, washing the catalyst residue twice with methanol. Combined methanol washings were concentrated under reduced pressure to yield 2 (0.506 g, 99%). The reaction was analysed by GC-MS which showed a conversion to product of >99%.

For comparison we measured the Ni content in the Ra—Ni catalysed reaction (Table 2) which showed more than ten times the Ni content in the solid, demonstrating the low release of Ni from Ni EnCat.

TABLE 4

Metal content in Ni EnCat and Ra—Ni Hydrogenation

| Temperature ° C. | Catalyst | Ni loading wt % | Conversions 1 | Conversions 2 | Ni content |
|---|---|---|---|---|---|
| 45 | Ni EnCat | 6.5 | <1% | >99% | 39 ppm |
| 45 | Ra—Ni | 50 | <1% | >99% | 421 ppm |

EXAMPLE 9

Reuse of Ni EnCat in Reduction of 4-chlorobenzonitrile

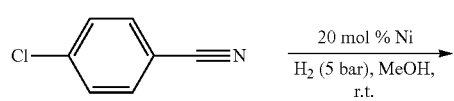

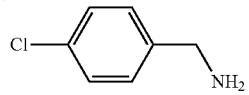

Activated Ni EnCat (0.26 g, water wet, 20 mol % Ni on substrate) was washed with MeOH three times to remove water and added to 4-chlorobenzonitrile (0.137 g, 1 mmol) dissolved in 7 N ammonia in MeOH (4 ml) in a pressure vessel. The vessel was sealed and purged twice with hydrogen then pressurised to 5-6 bar with hydrogen and the contents magnetically stirred at room temperature. After 22 h the hydrogen was vented and GCMS analysis showed complete consumption of the starting material and a product purity of 82%. The product mixture was removed from the Ni EnCat beads by decantation and the catalyst was washed with methanol (3×4 ml). Fresh 4-chlorobenzonitrile (0.137 g, 1 mmol) and 7 N ammonia in MeOH (4 ml) were added to the catalyst reaction mixture stirred in a pressure vessel as previously. After 22 h the hydrogen was vented and analysis of reaction by GCMS showed complete consumption of the starting material and a product purity of 65%.

COMPARATIVE EXAMPLE 5

Reuse of Sponge Nickel Catalyst

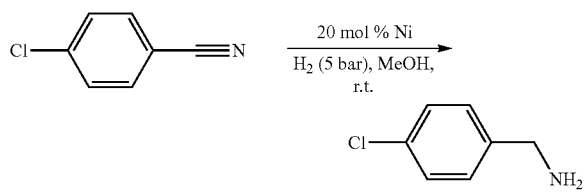

Sponge nickel from Comparative Example 1 (30 mg of a 50% wet slurry, 20 mol % Ni on substrate) was washed with MeOH three times to remove water and added to 4-chlorobenzonitrile (0.137 g, 1 mmol) dissolved in 7 N ammonia in MeOH (4 ml) in a pressure vessel. The vessel was sealed and purged twice with hydrogen then pressurised to 5-6 bar with hydrogen and the contents magnetically stirred at room temperature. After 22 h the hydrogen was vented and analysis of reaction by GCMS showed complete consumption of the starting material. The product solution was removed from the catalyst by decantation and the catalyst was washed with methanol (3×4 ml). Fresh 4-chlorobenzonitrile (0.137 g, 1 mmol) and 7 N ammonia in MeOH (4 ml) were added to the catalyst reaction mixture stirred in a pressure vessel as previously. After 22 h the hydrogen was vented and analysis of reaction by GCMS showed only 68% of the starting material was consumed and several by-products had been formed (16% product purity).

EXAMPLE 10

Ni EnCat Activity Lifetime

Activated Ni EnCat (0.26 g, 60% water wet, 15 mol % Ni on substrate) was washed with MeOH three times to remove water and added to 4-chlorobenzonitrile (0.137 g, 1 mmol) dissolved in 7 N ammonia in MeOH (4 ml) in a pressure vessel. The vessel was sealed and purged twice with hydrogen then pressurised to 5-6 atm with hydrogen and the contents magnetically stirred at room temperature. After 18 h the hydrogen was vented and the Ni EnCat beads removed by filtration. A sample of reaction mixture was then analysed by GCMS.

TABLE 5

| Time | GCMS Result | |
|---|---|---|
| | Conversion (%) | Purity (%) |
| Fresh Catalyst | >99 | 77 |
| 2 months | >99 | 72 |
| 4 months | >99 | 75 |
| 6 months | >99 | 54 |

This experiment shows that the catalyst retains activity over a 6 month period.

EXAMPLE 11

Mechanical Stability of Ni EnCat

The mechanical stability of Ni EnCat product has been tested by subjecting the beads to magnetic stirring whilst suspended in various solvents for 7 days.

Activated Ni EnCat beads (1 g) were weighed into 50 ml tubes from a Radleys Carousel reactor. 15 ml of the test solvent was then added to the reactor tubes and the mixture stirred using cross-type magnetic follower. After 7 days, samples of the catalyst were taken for evaluation by optical microscopy, and the solvents were filtered through a 0.45 micron filter. The filtrates from the experiments were then analysed for Nickel and Aluminium content via inductively coupled plasma (Table 6).

TABLE 6

| Solvent | Ni (ppm) | Al (ppm) |
|---|---|---|
| Acetone | <5 | <2 |
| 2-Propanol | <5 | <2 |
| Toluene | <5 | <2 |
| Water | <5 | <2 |

After 7 days stirring at high agitation speeds, optical microscope examination of the beads show no sign of attritional or chemical degradation. This is also demonstrated by very low metal leaching levels in each of the test solvents.

EXAMPLE 12

Ni EnCat Safety Benefits

The following have been addressed through hazard testing measurements on activation Ni EnCat. Tests carried out were:
UN Self-heating Solids—Basket Test
UN Test N.2: Pyrophoric Solids Test The Basket Test is conducted to define whether a material exhibits self-heating properties and, if so, to designate the transportation classification and packaging class. The sample container is housed in the centre of an oven and the oven temperature is raised to 140° C. and held isothermally for 24 hours. The temperature of the sample and oven are continually monitored/recorded. A positive result is denoted by a 60° C. rise in temperature over the oven temperature within 24 hours.

With a basket size of 100 mm and a test temperature of 140° C. it was determined that Ni EnCat should be classified as 'Not a selfheating substance of Class 4, Division 4.2'.

The pyrophoricity test was conducted to define whether the solid will ignite in contact with air. 1-2 ml of powdery substance to be tested were poured from about 1 m height onto a non-combustible surface. Observations were made as to whether the substance ignites during dropping or within 5 minutes of settling. This procedure is performed six times, unless a positive result is obtained. If the sample ignites in one of the tests, the material should be considered pyrophoric and should be classified in Packing Group I of Division 4.2.

The water was poured off Ni EnCat and the powder was allowed to dry on a filter paper for approximately 5 minutes, prior to testing. The drop test was repeated 6 times with no ignition in each case. It has been determined that Ni EnCat should be classified as 'Not a pyrophoric solid of Class 4.2'.

Separately the Ni EnCat sample dried under nitrogen, prior to testing. The drop test was repeated 6 times with no ignition in each case. It has been determined that Ni EnCat should be classified as 'Not a pyrophoric solid of Class 4.2'.

It can therefore be seen that the catalysts of the invention allow reactions to be conducted in high yield in a repeatable and reliable manner. The resulting products obtained are consistent with expectations based on the chemistries involved. Thus the catalysts not only overcome the problems of prior art systems but also have performance benefits.

The invention claimed is:

1. A microencapsulated metal catalyst system, the catalyst system comprising:
at least one metal and/or at least one metal alloy and a polymeric microsphere which is permeable to liquid,
wherein the at least one metal and/or metal alloy is retained inside the polymeric microsphere, thereby providing a metal catalyst encapsulated in the microsphere;
wherein the at least one metal and/or metal alloy is not associated with or bound to a ligand;
wherein the metal catalyst encapsulated in the microsphere is in the form of a sponge; and
wherein (i) the at least one metal is selected from the group consisting of: nickel, copper, cobalt, and iron, and (ii) the metal alloy comprises at least one metal selected from the group consisting of: nickel, copper, cobalt, and iron.

2. The metal catalyst system as claimed in claim 1, wherein the at least one metal is nickel or wherein the metal alloy includes nickel.

3. The metal catalyst system as claimed in claim 1, wherein a loading of the microencapsulated at least one metal or metal alloy is in the range of from 1 wt % to 40 wt %, where loading is based on the mass of metal or metal alloy to mass of the polymeric microsphere.

4. The metal catalyst system as claimed in claim 1, wherein the material used to form the walls of the microsphere is selected from the group consisting of a monomer, an oligomer, and a pre-polymer.

5. The metal catalyst system as claimed in claim 1, wherein the polymeric microsphere is a polyurea or a urea-formaldehyde polymer.

6. The metal catalyst system as claimed in claim 5, wherein the polymeric microsphere is a polyurea formed from polymethylene polyphenylene isocyanate and/or tolylene diisocyanate.

* * * * *